(12) United States Patent
Asada et al.

(10) Patent No.: US 8,808,146 B2
(45) Date of Patent: Aug. 19, 2014

(54) ACTIVITY METER

(75) Inventors: Yuji Asada, Kyoto (JP); Yoshitake Oshima, Kyoto (JP); Naoki Takeishi, Toyonaka (JP); Hiroshi Ogawa, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/985,093

(22) PCT Filed: Dec. 15, 2011

(86) PCT No.: PCT/JP2011/079038
§ 371 (c)(1),
(2), (4) Date: Aug. 13, 2013

(87) PCT Pub. No.: WO2012/117644
PCT Pub. Date: Sep. 7, 2012

(65) Prior Publication Data
US 2013/0328695 A1    Dec. 12, 2013

(30) Foreign Application Priority Data
Mar. 1, 2011   (JP) ................. 2011-043991

(51) Int. Cl.
*A63B 71/00*   (2006.01)
*A61B 5/22*    (2006.01)
*A61B 5/11*    (2006.01)
*A61B 5/00*    (2006.01)

(52) U.S. Cl.
CPC ............... *A61B 5/0002* (2013.01); *A61B 5/22* (2013.01); *A61B 5/6838* (2013.01); *A61B 5/11* (2013.01)
USPC ............... 482/8; 600/595; 600/547; 600/531; 340/539.11; 340/539.12; 340/870.02

(58) Field of Classification Search
CPC .. A61B 5/0537; A61B 5/4869; A61B 5/4872; A61B 5/02438; A61B 5/1118; G01G 19/50; A63B 2230/75
USPC .......... 600/300, 301, 500, 547, 595; 128/898; 340/870.01, 870.02, 539.11, 539.12; 482/8; 702/19, 127–199
See application file for complete search history.

(56) References Cited

U.S. PATENT DOCUMENTS

| 2006/0094978 | A1  | 5/2006 | Kodama |
| 2009/0204018 | A1* | 8/2009 | Tseng et al. .................. 600/547 |
| 2010/0130890 | A1* | 5/2010 | Matsumura et al. .......... 600/595 |

FOREIGN PATENT DOCUMENTS

| JP | 2001-258870 A | 9/2001 |
| JP | 2003-024293 A | 1/2003 |
| JP | 2006-204446 A | 8/2006 |
| JP | 2007-089699 A | 4/2007 |
| JP | 2010-017525 A | 1/2010 |

OTHER PUBLICATIONS

Official Communication issued in International Patent Application No. PCT/JP2011/079038, mailed on Mar. 13, 2012.

* cited by examiner

*Primary Examiner* — Nabil Syed
*Assistant Examiner* — Jerold Murphy
(74) *Attorney, Agent, or Firm* — Keating & Bennett, LLP

(57) ABSTRACT

An activity meter includes an activity amount acquisition unit that acquires an amount of physical activity of a user, an activity age acquisition unit that acquires an activity age representing a standard age of a person who does a same amount of activity as the activity amount acquired in a unit period, using body information and a basal metabolic rate of the user, and an output processing unit that outputs information relating to the acquired activity age.

10 Claims, 7 Drawing Sheets

(A)

(B)

ACTIVITY METER

BACKGROUND OF THE INVENTION

1. Field of the Invention

The present invention relates to an activity meter that measures an amount of physical activity of a user, and more particularly to an activity meter that converts the amount of physical activity to an activity age and outputs the activity age.

2. Description of the Related Art

For activity meters, JP 2006-204446A and JP 2001-258870A show methods for measuring the exercise intensity of physical activity or the calories burned during physical activity utilizing an acceleration sensor. With the activity meter of JP 2006-204446A, a standard deviation Sw of acceleration in a fixed time period tw is computed from the output signal of the acceleration sensor, and an exercise intensity wi is computed from the standard deviation Sw using a conversion equation formulated in advance. Also, with the device of JP 2001-258870A, the impulse of momentum is calculated by vector synthesis from tri-axial acceleration, and energy expenditure is calculated from the impulse in response to the type of exercise. The type of exercise is determined based on the ratio between the impulse calculated by vector synthesis and the impulse in the depth, horizontal and vertical directions.

In JP 2010-17525A, the age activity pattern that the user's state of activity is equivalent to is computed by comparing the energy expenditure history with reference data.

Although the activity meters of JP 2006-204446A and JP 2001-258870A output the user's activity amount as calories burned, it is unclear whether the amount of calories burned is high or low in comparison with a person of the same age or to a person of what age that amount of calories burned is equivalent.

Although the age activity pattern to which the user's state of activity is equivalent is computed in JP 2010-17525A, the amount of calories burned differs with age even for the same state of activity, and thus it is not appropriate to simply compare calories burned with a person of the same age like in JP 2010-17525A.

SUMMARY OF THE INVENTION

Preferred embodiments of the present invention provide an activity meter that acquires information relating to a more reliable activity age from an amount of physical activity of a user.

An activity meter according to a preferred embodiment of the present invention is provided with an activity amount acquisition unit that acquires an amount of physical activity of a user, an acquisition unit that acquires an activity age representing a standard age of a person who does the same amount of activity as the activity amount acquired in a unit period, using body information and a basal metabolic rate of the user, and an output unit that outputs information relating to the activity age.

According to preferred embodiments of the present invention, information relating to a more reliable activity age can be acquired from the amount of physical activity of a user by using the user's own basal metabolic rate.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
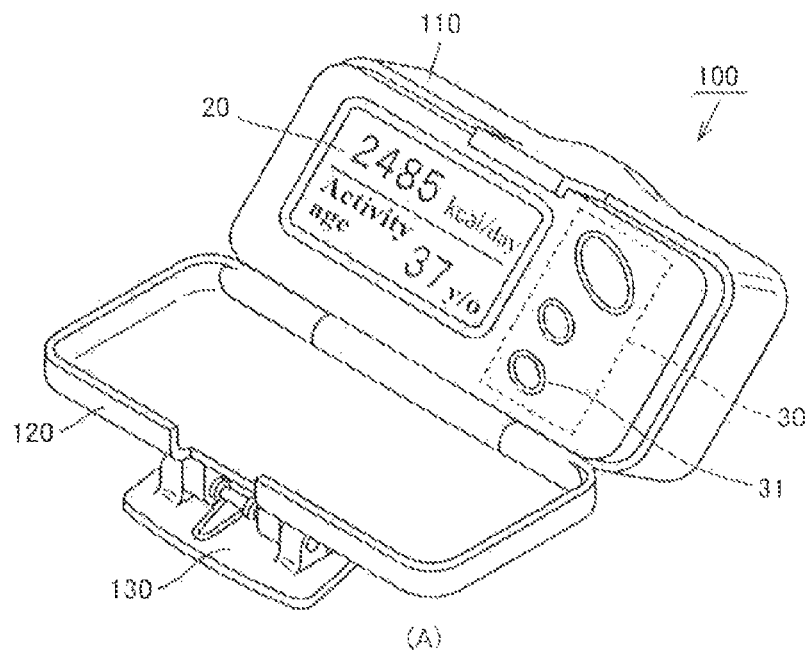
FIGS. 1A and 1B are diagrams illustrating the external appearance and a mode of wearing a pedometer according to a preferred embodiment of the present invention.
Figure 1:
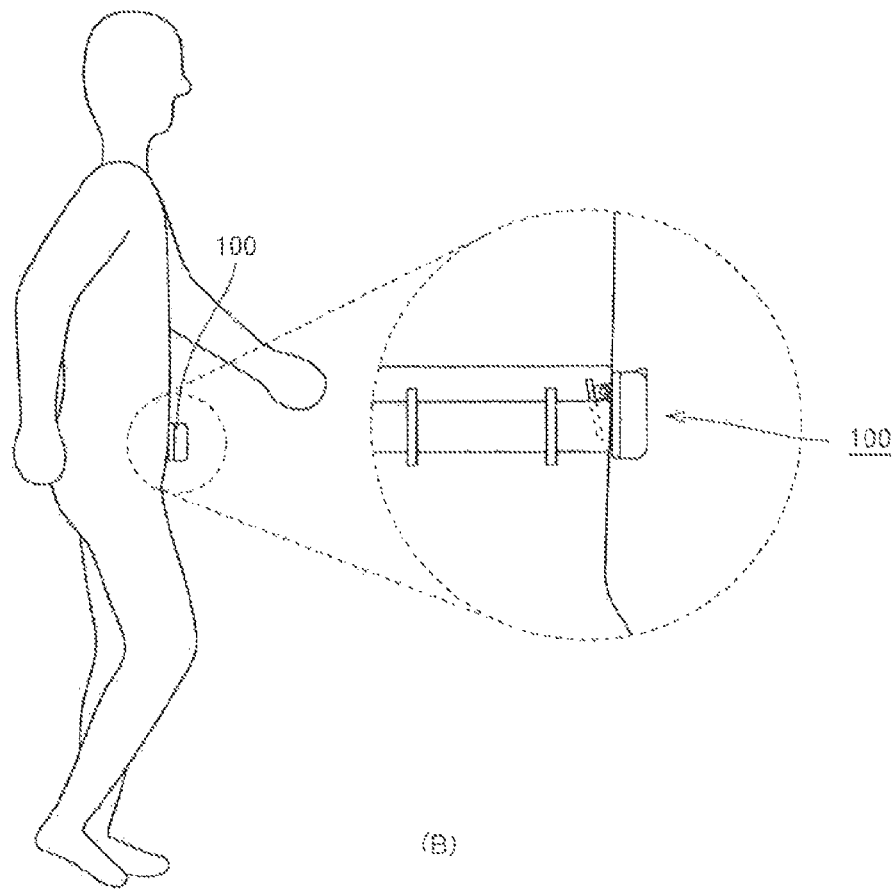

Hereinafter, preferred embodiments of the present invention will be described in detail with reference to the drawings. Note that the same or corresponding portions in the following preferred embodiments are given the same reference signs in the drawings, and description thereof will not be repeated.

In the present preferred embodiment, "activity age" represents a standard (or average) age of persons who, in a predetermined period, burn the total amount of calories burned by the user when active for the same period. Here, the predetermined period is preferably 1 day, for example, but any other desirable time period could be used instead.

Also, "real age" preferably indicates calendar age (age counted from the time of birth).

In the present preferred embodiment of the present invention, METs (Medical Evangelism Training & Strategies) are preferably used as an index indicating physical activity intensity. METs are a unit representing the intensity of physical activity in multiples of a resting state, with sitting down quietly being equivalent to 1 METs and normal walking being equivalent to 3 METs.

Also, "exercise (Ex)" is a unit representing the amount of physical activity, and is obtained by multiplying the intensity of physical activity (METs) by the implementation time period (time: hour) of physical activity.

In the present preferred embodiment of the present invention, a pedometer is illustrated as the activity meter, but the activity meter is not limited to being a pedometer. In other words, the activity meter can be any device having a function capable of measuring the activity amount resulting from physical activity including exercise and daily activities (e.g., vacuuming, carrying items, cooking, etc.). Although a pedometer can be shared by two or more persons, it is assumed here for ease of description that the pedometer is used by one person.

Referring to FIG. 1A, a pedometer 100 serving as an activity meter preferably includes a compact main body casing that is portable, and the main body casing is divided into a case main body 110, a cover body 120, and a clip body 130.

The case main body 110 preferably includes a display surface on which is provided a display 20 arranged to display various information such as, for example, the counted number of steps, activity intensity and activity age, and an operation unit 30 including various buttons arranged to receive operations by the user. The operation unit 30 preferably includes a button 31 that the user operates in order to request output of the activity age.

The bottom end of the case main body 110 and the cover body 120 are rotatably coupled around a joining portion, and the pedometer 100 is opened and closed by rotation of this joining portion. The clip body 130 is preferably provided on an opposite surface of the cover body 120 to the surface facing the display surface of the case main body 110. The clip body 130 enables the pedometer 100 to preferably be worn on the user's waist, abdomen, or the like as shown in FIG. 1B.

Figure 2:
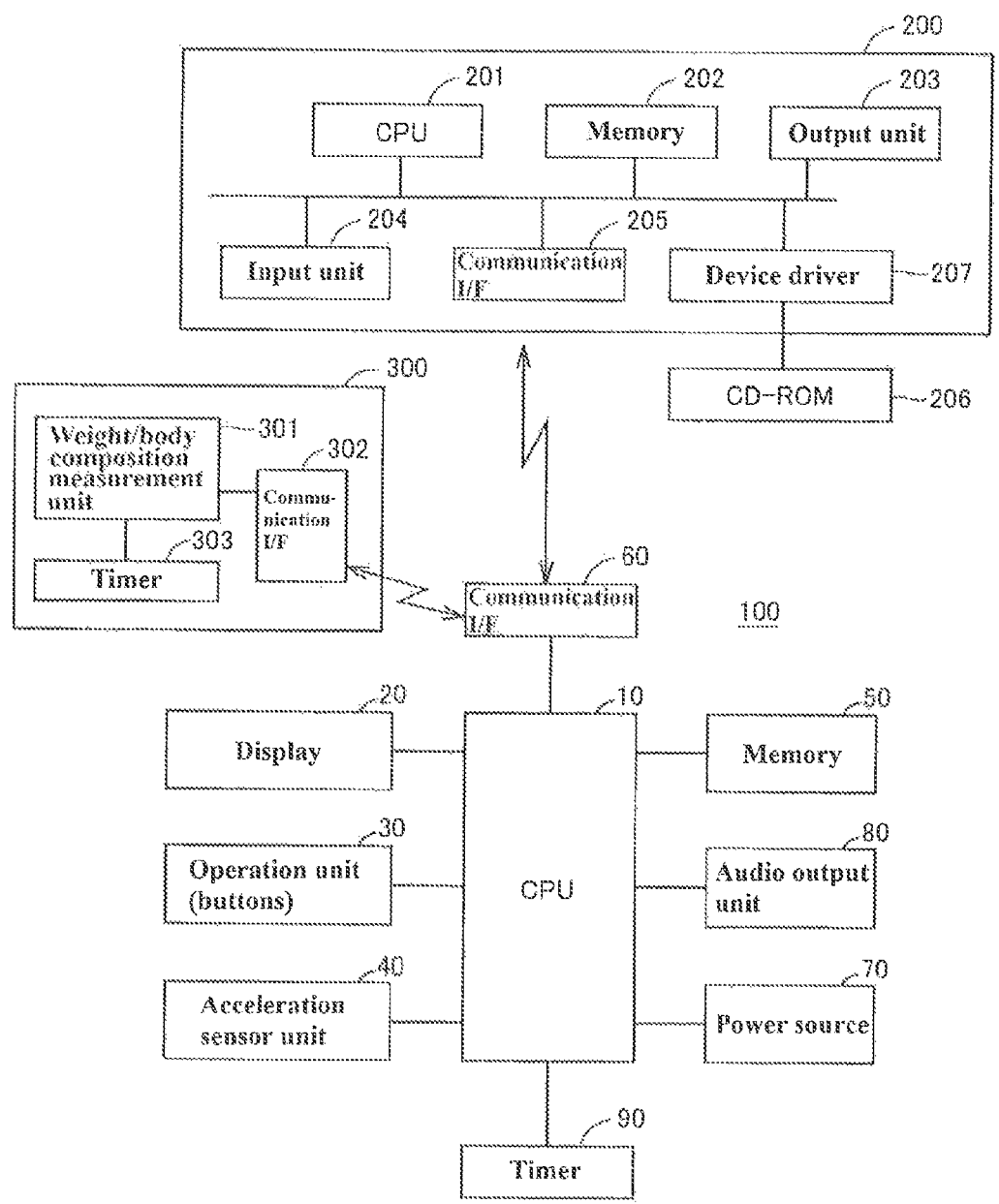
FIG. 2 is a diagram showing the hardware configuration of a system that includes a pedometer according to a preferred embodiment of the present invention.

Referring to FIG. 2, a hardware configuration will be described with reference to a system including the pedometer 100. The pedometer 100 preferably includes, as an exemplary hardware configuration, a CPU (Central Processing Unit) 10 arranged and programmed to perform overall control, the display 20, the operation unit 30, an acceleration sensor unit 40 including an acceleration sensor and an MPU (Micro-Processing Unit), a memory 50 arranged to store programs that are executed by the CPU 10, data and the like, a communication I/F (abbreviation of "interface") 60 arranged to permit wireless or wired communication with an external device, a power source 70 such as, for example, a battery, an audio output unit 80 arranged to output audio, and a timer 90 that measures time and outputs time data.

The pedometer 100 preferably performs wireless or wired communication with external devices 200 and 300 via the communication I/F 60. The device 200 is preferably equivalent to a mobile terminal (PDA (Personal Digital Assistant), mobile phone, etc.) or a stand-alone computer, for example, and the device 300 preferably has a function of measuring the user's weight and body composition.

The device 200 preferably includes a CPU 201, a memory 202, an output unit 203, an input unit 204, a communication I/F 205, and a device driver 207 arranged to access data in a CD-ROM (Compact Disk Read Only Memory) 206. The device driver 207 preferably includes the CD-ROM 206 removably loaded therein, and reads out data (including programs) from the loaded CD-ROM 206 or writes data to the loaded CD-ROM 206.

The device 300 preferably includes a weight/body composition measurement unit 301 that measures the user's height, weight, body fat, and the like, a communication I/F 302 arranged to transmit measured information outside the device, and a timer 303. Measured weight and body composition information is transmitted to the pedometer 100 via the communication I/Fs 302 and 60, as weight data and body composition data to which time data indicating the measurement time clocked by the timer 303 is respectively added. The timer 303 and the timer 90 are adjusted so as to perform synchronized clocking operations.

Figure 3:
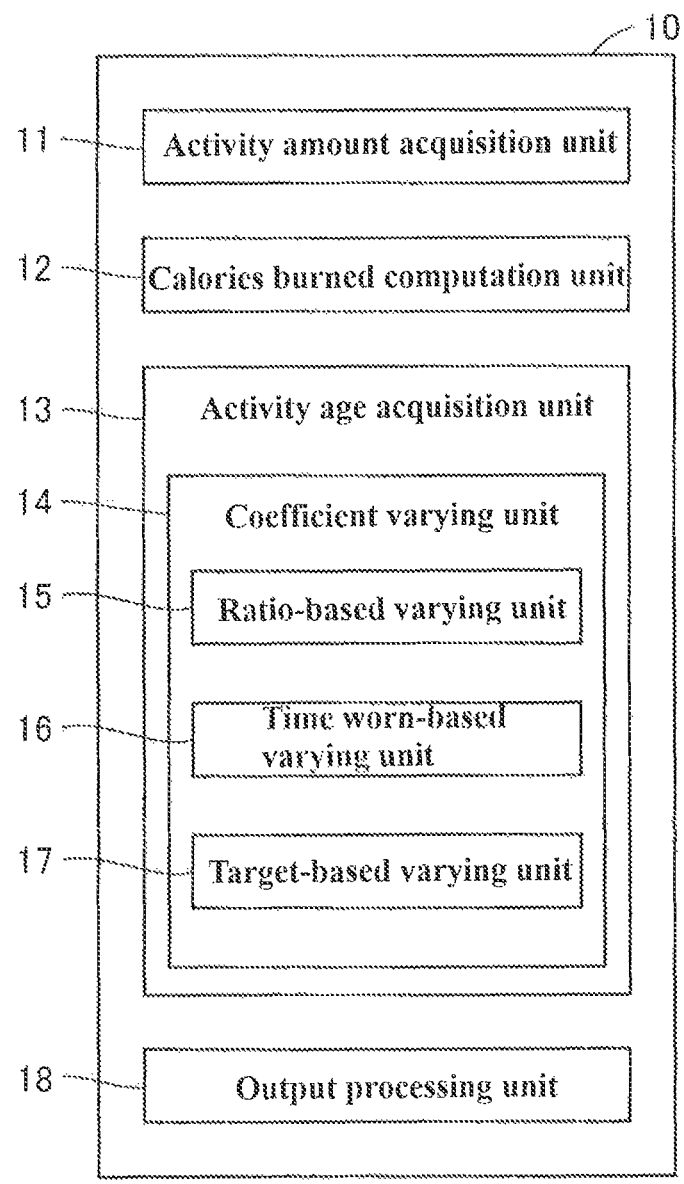
FIG. 3 is a diagram showing the functional configuration of a pedometer according to a preferred embodiment of the present invention.

The configuration of functions that preferably operate under the control of the CPU 10 is shown in FIG. 3. The functions preferably include an activity amount acquisition unit 11 arranged and programmed to acquire the amount of physical activity of the user, a calories burned computation unit 12 arranged and programmed to compute the total calories burned in the predetermined period based on the acquired activity amount, an activity age acquisition unit 13 arranged and programmed to compute the activity age from the computed calories burned in the predetermined period, and an output processing unit 18 arranged and programmed to output various information including activity age and the like to outside the device. These units correspond to a program provided on a non-transitory computer readable medium to be executed by a computer or processing device, a combination of a program and a circuit module, or purely hardware.

Computation of Calories Burned Based on Activity Amount

The activity amount acquisition unit 11 preferably receives input of activity intensity from the acceleration sensor unit 40 and input of time data from the timer 90. Activity intensity data Mi (discussed later) obtained by associating the activity intensity from the acceleration sensor unit 40 and the time data from the timer 90 is acquired, and the acquired activity intensity data Mi is stored in the memory 50. The time data associated with the activity intensity indicates the implementation date and time of the exercise for which the activity intensity was measured.

The acceleration sensor unit 40 preferably measures the number of steps in a manner similarly to a measurement of the number of steps performed by a generic pedometer. The acceleration sensor detects acceleration applied to the pedometer 100. The detected acceleration is preferably derived as a voltage signal. The MPU processes the output signal from the acceleration sensor. For example, the MPU performs processing so as to count each time an acceleration of greater than or equal to a threshold is detected as one step, based on the signal output sequentially from the acceleration sensor.

The measurement operation performed by the MPU of the acceleration sensor unit 40 involves computing the activity intensity (unit: METs) per unit period, using acceleration data measured based on the acceleration signal input from the acceleration sensor, with predetermined time intervals (e.g., 20-second intervals, etc.) defined in advance as the unit period. As a specific computation method, the activity intensity can be computed using a well-known technique, such as the technique disclosed in JP 2009-28312A.

Activity intensity is an index representing the intensity of physical activity that depends on walking pitch (number of steps per unit period) and the height of the user that is input in advance. For example, a resting state is equivalent to 1 METs, walking normally (4 km/h) is equivalent to 3 METs, vacuuming is equivalent to 3.5 METs, and jogging is equivalent to 7 METs (from: Exercise and Physical Activity Guide for Health Promotion "Exercise Guide 2006" (Ministry of Health, Labour and Welfare)).

The calories burned computation unit 12 is preferably arranged and programmed to compute the calories burned by the user exercising according to the following equation: calories burned (kcal)=activity intensity (METs)×weight (kg)× activity duration (hour)×1.05 (from: Exercise and Physical Activity Guide for Health Promotion "Exercise Guide 2006", Ministry of Health, Labour and Welfare). Activity intensity and activity duration can be acquired from the activity intensity data Mi, and weight can be acquired from physique data 57 discussed later.

The conversion equation that is used by the activity age acquisition unit 13 preferably includes parameters (variables) and coefficients. Parameters include the basal metabolic rate of the user. The activity age acquisition unit 13 preferably includes a coefficient varying unit 14 arranged and programmed to variably determining coefficients. The coefficient varying unit 14 preferably includes a ratio-based varying unit 15, a time worn-based varying unit 16, and a target-based varying unit 17. The ratio-based varying unit 15 variably determines coefficients such that the ratio between the amount of fluctuation in the calories burned and the amount of fluctuation in the activity age computed in response to the amount of fluctuation in the calories burned will be a value in a predetermined range. The time worn-based varying unit 16 variably determines coefficients in accordance with the length of time that the pedometer 100 is worn. The target-based varying unit 17 variably determines coefficients using a target activity amount for the predetermined period.

Figure 4:
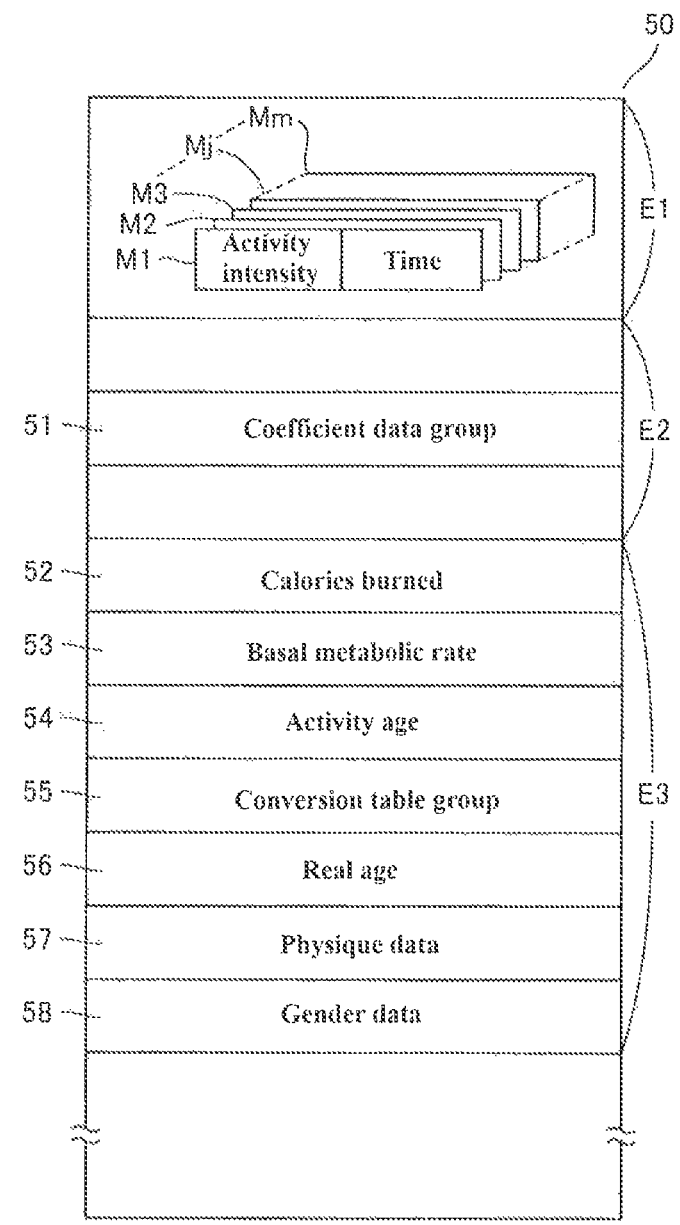
FIG. 4 is a diagram showing exemplary memory content of a memory according to a preferred embodiment of the present invention.

The storage content of the memory 50 is illustrated in FIG. 4. Referring to FIG. 4, the memory 50 preferably includes an area E1 where the activity intensity data Mi (i=1, 2, 3, . . . j, . . . m) is stored, an area E2 where a coefficient data group 51 that consists of different types of coefficients that are used in the conversion equation to convert total calories burned into an activity age is stored, and an area E3. The coefficients in the coefficient data group 51 are assumed to have been computed in advance through testing and stored.

The activity intensity data Mi includes measured activity intensity and a measurement time period indicating the time period for which the activity was implemented. The values of the coefficients in the coefficient data group 51 can be variably set by a user operation via the operation unit 30.

The area E3 preferably includes computed calories burned 52 for the user, a computed basal metabolic rate 53 and a computed activity age 54, and further has stored therein a conversion table group 55 that is referenced in order to convert computed calories burned into an activity age, real age data 56 of the user, physique data 57 including the user's weight, height and the like, and gender data 58 indicating the gender of the user stored therein. Here, the real age 56, the physique data 57, and the gender data 58 represent body information relating to the user's body.

Figure 5:
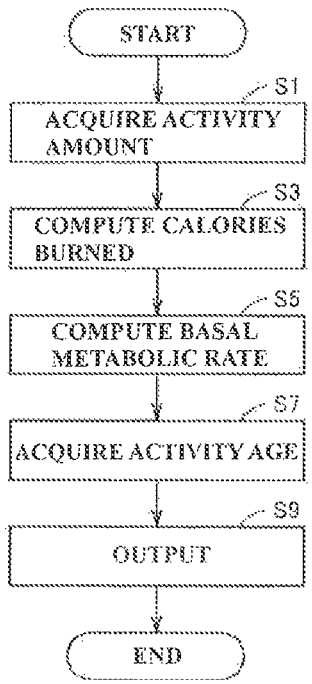
FIG. 5 is a processing flowchart according to a preferred embodiment of the present invention.

A processing flowchart according to the present preferred embodiment is shown in FIG. 5. Processing according to this processing flowchart is preferably realized by the CPU 10 reading out a predetermined program from the memory 50 and executing the instructions of the read program. Computation of the user's activity age will be described according to the flowchart of FIG. 5. Note that it is assumed that a sufficient number of sets of activity intensity data Mi are stored in the area E1 of the memory 50.

When the user operates the button 31 of the operation unit 30, the CPU 10 receives the operation. Specifically, based on the operation signal output from the operation unit 30 as a result of the button 31 being operated, the CPU 10 starts the processing of FIG. 5. When the processing has been started, the activity amount acquisition unit 11 preferably acquires the activity amount of the predetermined period, based on the activity intensity data Mi read out from the area E1 of the memory 50 (step S1). Subsequently, the calories burned computation unit 12 computes the total calories burned of the user for the predetermined period, based on the acquired activity amount (step S3), and the CPU 10 computes the basal metabolic rate of the user for the predetermined period (step S5).

The activity age acquisition unit 13 preferably computes the activity age, in accordance with a predetermined conversion equation using the computed total calories burned and basal metabolic rate and coefficients of the coefficient data group 51 (step S7). The computed activity age is stored in the memory 50 together with being provided to the output processing unit 18. The output processing unit 18 displays information relating to the provided activity age on the display 20 or outputs the information via the audio output unit 80 (step S9). This preferably ends the processing.

An exemplary display is shown in FIG. 1A. In FIG. 1A, the computed calories burned for 1 day, for example, is displayed together with the computed activity age. The user is able to judge that the amount of activity (exercise) is appropriate if the displayed activity age indicates the real age or is close to the real age, and is able to judge that the amount of activity (exercise) is insufficient if the displayed activity age greatly exceeds the real age. Accordingly, the user knows whether the amount of calories burned is high or low compared with a person of the same age, and to a person of what age his or her amount of calories burned is equivalent, and is able to gain the motivation to continue the appropriate amount of activity (exercise).

The information relating to activity age that is output is not limited thereto. For example, a value (for example, +5 years old, etc.) obtained by subtracting the activity age from the real age or information indicating the age group (for example, twenties, etc.) to which the activity age belongs may be output.

Basic Method of Computing Activity Age

In the activity age computation (step S7), the activity age is preferably computed in accordance with the following basic procedure. First, derivation of the computation equation that defines the basis for computing activity age will be described.

The theoretical basal metabolic rate of the user for 1 day can be computed by equation (1). Equation (1) is proposed in Ganpule A A, et al. Interindividual variability in sleeping metabolic rate in Japanese subjects, European Journal of Clinical Nutrition (2007), pp. 1-6.

$$\text{theoretical basal metabolic rate} = (0.0481 \times W + 0.0234 \times H - 0.0138 \times R - 0.5473 \times F + 0.1238) \times 239 \tag{1}$$

where W denotes weight, H denotes height, R denotes real age, and F denotes gender. Weight W is denoted in kilograms (kg) and height H is denoted in centimeters (cm). F is 1 if the gender is male and is 2 if the gender is female. Following from equation (1), real age: R can be represented by equation (2).

Here, although the basal metabolic rate is computed in accordance with an arithmetic equation, the arithmetic equation is not limited to equation (1), and may be another arithmetic equation. Also, the type and value of the parameters used in the computation equation are not limited to those shown in equation (1), and a configuration may be adopted in which the basal metabolic rate is computed from biological information and the type and value of the parameters is determined empirically from the computed basal metabolic rate, for example.

$$R = (\text{theoretical basal metabolic rate}/239 - 0.1238 - 0.0481 \times W - 0.0234 \times H + 0.5473 \times F)/(-0.0138) \tag{2}$$

Here, it is known that the physical activity level PAL for 1 day can be computed from total calories burned (unit: kcal) for 1 day/basal metabolic rate (unit: kcal) for 1 day, and that the physical activity level PAL is 1.60 to 1.90 for a "normal" amount of activity. Here, the intermediate value 1.75 is employed as the representative value. Accordingly, because a relational equation: total calories burned [kcal/day] at standard level=theoretical basal metabolic rate [kcal/day]×1.75 is satisfied, relative basal metabolic rate=actual total calories burned/1.75 (eq. (3)) can be derived from this relational equation, in order to derive the activity age of the user. "Actual total calories burned" indicates the total calories burned computed at step S3. Following from equations (1) to (3), equation (4) that defines the basis for computing activity age has be derived.

$$\text{Activity age [age]} = \{(\text{actual total calories burned [kcal/day]}/1.75)/239 - 0.1238 - 0.0481 \times W - 0.0234 \times H + 0.5473 \times F\}/(-0.0138) \tag{4}$$

The activity age acquisition unit 13 computes the user's activity age by substituting the values of the total calories burned for 1 day computed at step S3, the physique data 57 and the gender data 58 into equation (4), and performing an arithmetic operation in accordance with equation (4).

The activity age may be alternatively acquired by being readout from a table, instead of an arithmetic operation in accordance with equation (4), if so desired. In other words, the activity age acquisition unit 13 acquires the activity age by searching a table in the conversion table group 55, instead of an arithmetic operation that uses the abovementioned equation (4).

Here, a conversion table is included in the conversion table group 55 for each set of actual age R, height H, weight W and gender F. In the conversion table corresponding to each set, an activity age is stored in association with a value of the basal metabolic rate computed in accordance with equation (3).

Figure 6:
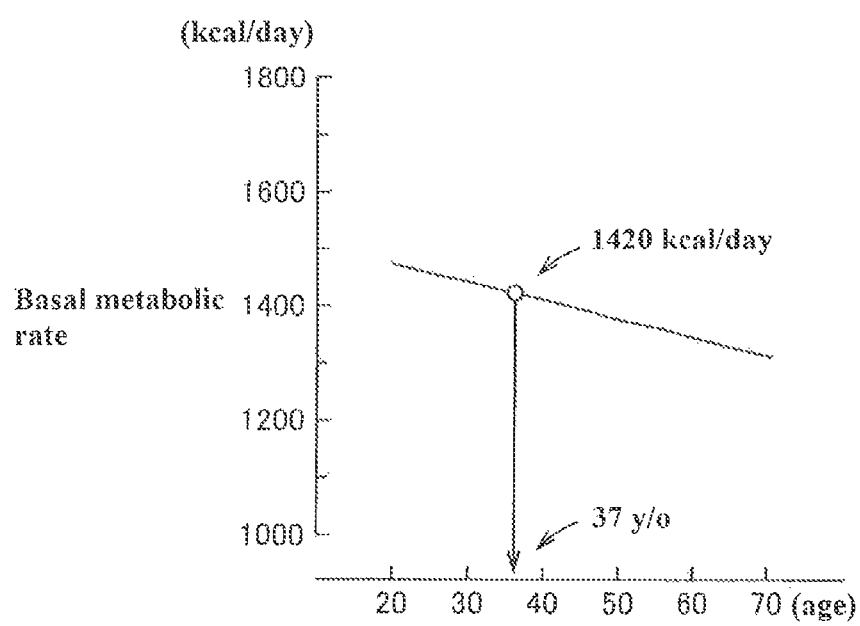
FIG. 6 is a diagram showing an example of a conversion table according to a preferred embodiment of the present invention.

An exemplary conversion table is shown in FIG. 6. In FIG. 6, a conversion table in the case where the height, weight and gender of the user are respectively 170 cm, 60 kg and male is shown as a linear function graph in which activity age is shown on the horizontal axis and basal metabolic rate computed by equation (3) is shown on the vertical axis. The activity age acquisition unit 13 searches the conversion table group 55 based on the physique data 57 and the gender data 58 in the memory 50, and reads out a corresponding conversion table (FIG. 6). Also, the activity age acquisition unit 13 preferably computes the basal metabolic rate from the total calories burned computed by the calories burned computation unit 12, based on equation (3).

For example, if the total calories burned is 2485 kcal, the basal metabolic rate is computed by equation (3) to be 1420 kcal. Searching the conversion table of FIG. 6 based on the basal metabolic rate (1420 kcal) enables the activity age acquisition unit 13 to acquire 37 y/o as the activity age of the user. Here, if a user's real age is 50 y/o, the user knows that his or her activity age is 13 years younger than his or her real age.

Note that the conversion table in FIG. 6 was computed on the basis of Ganpule A A, et al. Interindividual variability in sleeping metabolic rate in Japanese subjects, European Journal of Clinical Nutrition (2007), pp. 1-6.

Method of Computing Activity Age Based on Slope Correction

A more accurate activity age can be computed by modifying equation (4) that provides the basis of computing activity age, based on age-dependent differences in the basal metabolic rate.

In other words, according to the relationship between age and calories burned through activity in accordance with equation (4), the range of fluctuation in the activity age increases relative to the amount of fluctuation in the daily total calories burned. This is due to physical activity level PAL=1.75 being uniformly applied in equation (4) irrespective of age.

In view of this, the inventors found that, to compute the activity age, PAL, that is, the coefficients of the arithmetic operation, can be variably determined such that the ratio between the amount of fluctuation in the basal metabolic rate and the amount of fluctuation in the activity age computed in response to the amount of fluctuation in the basal metabolic rate is a value in a predetermined range.

It has been discovered that, to acquire an accurate activity age, physical activity level PAL=1.75x can be used such that the value fluctuates within a "normal" range for the physical activity level (PAL=1.60 to 1.90), or in other words, that equation (4) can be modified such as in equation (5) using correction coefficients k1 and k2. In equation (4), k1=1.9 and k2=43, for example.

$$\text{activity age} = \{(\text{total calories burned}/1.75)/239 - 0.1238 - 0.0481 \times W - 0.0234 \times H + 0.5473 \times F\}/(-0.0138 \times k1) + k2 \tag{5}$$

The ratio-based varying unit 15 is arranged and programmed to determine the correction coefficients k1 and k2. Here, because the coefficients k1 and k2 are stored in the coefficient data group 51 for each set of weight W, height H and gender F, the ratio-based varying unit 15 is able to read out the corresponding correction coefficients k1 and k2, by searching the coefficient data group 51 based on the weight and height in the physique data 57 and the gender data 58 of the user read out from the memory 50.

The activity age acquisition unit 13 is arranged and programmed to compute the activity age in accordance with equation (5) which uses the physical activity level PAL=1.75x. The computed activity age does not fluctuate greatly due to fluctuation in the total calories burned. This will be described with reference to the graph of FIG. 7.

Figure 7:
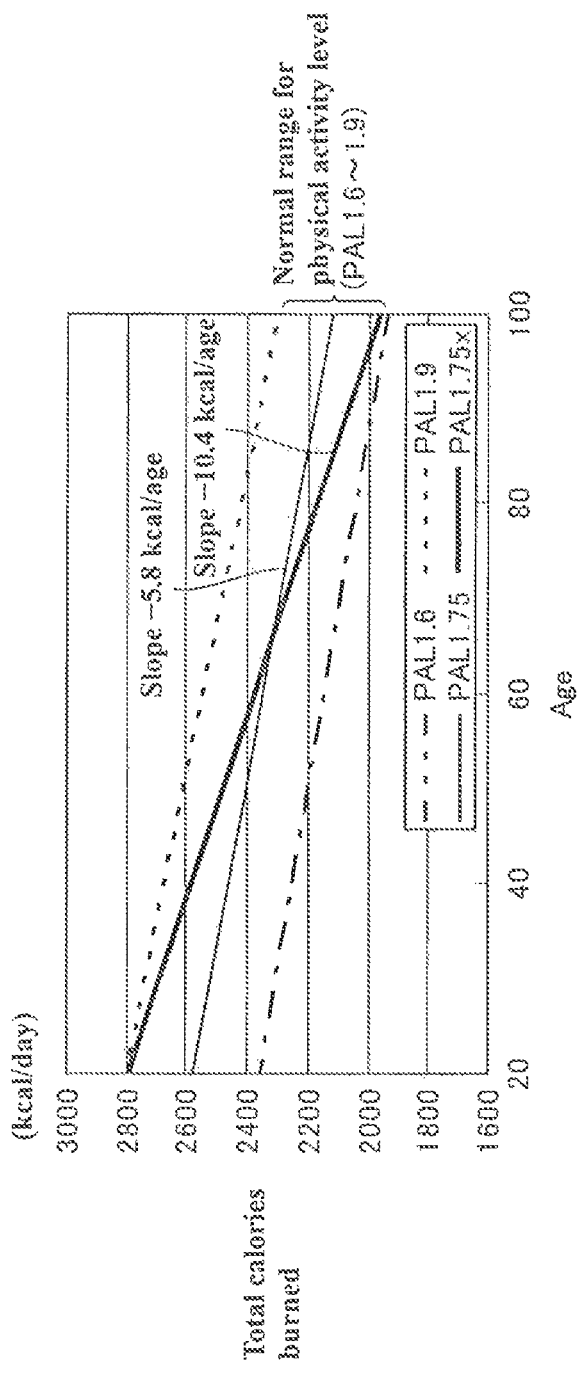
FIG. 7 is a graph illustrating computation of activity age according to a preferred embodiment of the present invention.

In the graph of FIG. 7, total calories burned for 1 day is shown in the vertical axis, and activity age is shown on the horizontal axis. The straight line (thick solid line in FIG. 7) of PAL 1.75x in the graph represents equation (5) in the case where the user's height, weight and gender are respectively 170 cm, 60 kg and male, and the straight line (thin solid line in FIG. 7) of PAL 1.75 represents equation (4). The ratio-based varying unit 15 variably sets the coefficients k1 and k2 such that the slope of the straight line of PAL 1.75x falls within a range from the straight line of PAL 1.6 to the straight line of PAL 1.9 in the case where the values of the equation shown by the straight line of PAL 1.75x are the same.

As shown in FIG. 7, the slope of the straight line of PAL 1.75 indicates −5.8 kcal/age whereas the slope of the straight line of PAL 1.75x indicates −10.4 kcal/age, and the amount of fluctuation in the activity age relative to the amount of fluctuation in the total calories burned can be suppressed to a low value following from the straight line of PAL 1.75x. Accordingly, a reliable activity age can be computed using equation (5), irrespective of the fluctuation in the total calories burned.

The activity age acquisition unit 13 may alternatively acquire the activity age by searching a table in the conversion table group 55, instead of an arithmetic operation that uses equation (5).

Here, a conversion table is preferably included in the conversion table group 55 for each set of height H, weight W, and gender F. In the conversion table corresponding to each set, an activity age is stored in association with a value of the total calories burned computed by the calories burned computation unit 12. For example, in FIG. 7, a conversion table in the case where the user's real age, height, weight and gender are respectively 50 y/o, 170 cm, 60 kg, and male is shown as the values of the linear function equation (5) indicated by PAL 1.75x in which activity age is shown on the horizontal axis and total calories burned is shown on the vertical axis.

Standardization by Real Age

The user's real age is not taken into consideration in the terms of the abovementioned equations (4) and (5) except for the correction coefficients. Thus, the activity age will be the same if the basal metabolic rate is the same (i.e., if calories burned is the same) irrespective of real age, which tends to result in an activity age that is not close to the real age.

In view of this, in order to acquire a more accurate activity age, the activity age acquisition unit 13 is preferably arranged and programmed to compute the activity age in accordance with an equation that allows the activity age to fluctuate depending on total calories burned, based on the user's real age. A conversion equation which computes the activity age from the total calories burned is illustrated below.

An activity age A is computed in accordance with equation (6), and equation (4) is applied if a value of (activity age A−real age) is between −10 and 9 inclusive, equation (7) is applied if this value is greater than or equal to 10, and equation (8) is applied if the value is less than −10, for example.

activity age $A$=real age+$k3$×{total calories burned−(1.75×basal metabolic rate)} (6).

activity age=real age+(activity age $A$−real age−10)/$k4$ (7).

activity age=real age+(activity age $A$−real age+10)/$k4$ (8).

Note that the coefficients k3 and k4 in the equations are values that are read out from the coefficient data group 51, and are k3=−0.087 and k4=2, for example. Here, because the coefficients k3 and k4 are stored in the coefficient data group 51 for each set of real age R, weight W, height H, and gender F, the coefficient varying unit 14 is able to read out the corresponding correction coefficients k3 and k4 by searching the coefficient data group 51 based on the user's real age, weight, height, and gender read out from the memory 50.

Figure 8:
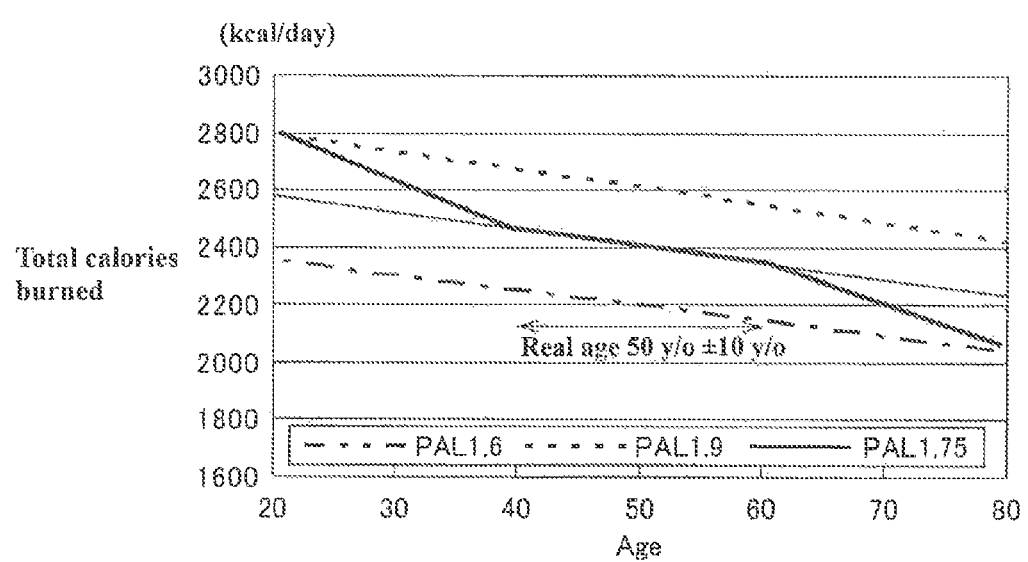
FIG. 8 is another graph illustrating computation of activity age according to a preferred embodiment of the present invention.

Equations (4), (7), and (8) will be described with reference to the graph of FIG. 8. In the graph of FIG. 8, calories burned for 1 day is shown on the vertical axis and activity age is shown on the horizontal axis. The straight line of PAL 1.75 (solid line in FIG. 8) in the graph represents equation (4) in the case where the user's real age, height, weight, basal metabolic rate, and gender are respectively 50 y/o, 170 cm, 60 kg, 1374 kcal, and male. Equation (4) is applied in an age range that is comparatively close to the real age of 50 y/o, such as a range of ±10 y/o, for example, and equation (7) or (8) having a slope greater than the slope of equation (4) is applied outside this range.

Accordingly, since the activity age fluctuates while linearly tracking the fluctuation in the total calories burned in an age range centered on the real age, the computed activity age tends to be comparatively close to the real age, and an index that is easy for the user to target can be obtained.

The activity age acquisition unit 13 may alternatively be arranged and programmed to acquire the activity age by searching a table in the conversion table group 55, instead of an arithmetic operation that uses the abovementioned equations (4), (7), and (8).

Here, a conversion table is included in the conversion table group 55 for each set of real age R, height H, weight W, basal metabolic rate, and gender F. In the conversion table corresponding to each set, an activity age is stored in association with a value of the total calories burned computed by the calories burned computation unit 12. For example, in FIG. 8, a conversion table in the case where the user's real age, height, weight, basal metabolic rate, and gender are respectively 50 y/o, 170 cm, 60 kg, 1374 kcal, and male is shown as the values of equations (4), (7), and (8) in which activity age is shown the horizontal axis and total calories burned is shown on the vertical axis.

Correction Based on Time Worn

In the present preferred embodiment of the present invention, the total calories burned for 1 day is used in order to compute the activity amount, but to accurately compute the calories burned for 1 day, the pedometer 100 needs to be worn for 24 hours. However, in practice, many users wear the pedometer 100 when they go out or while exercising but not at other times, and in the case of such a user, an accurate activity age cannot be computed even if the abovementioned conversion equations are applied, since the physical activity level PAL falls below "normal" (PAL=1.6 to 1.9). For example, the activity age tends to be high even on days where the user did some exercise, leading to a drop in the user's level of satisfaction.

In view of this, the time worn-based varying unit 16 variably changes the PAL value applied to a conversion equation for computing a time worn-based activity age, according to the length of time worn.

The time worn-based varying unit 16 is arranged and programmed to compute the time period for which an acceleration signal greater than or equal to a predetermined level is detected as the length of time that the pedometer 100 is worn. The unit time worn is time (h: hour). The PAL value to be applied is computed in accordance with equation (9).

PAL=1.75−$k5$×(24 [h]−time worn [h]) (9).

The coefficient k5 is read out from the coefficient data group 51. Here, because the coefficient k5 is stored in the coefficient data group 51 for each set of weight W, height H, and gender F, the time worn-based varying unit 16 is able to read out the corresponding correction coefficient k5, by searching the coefficient data group 51 based on the user's weight, height and gender read out from the memory 50.

By computing the activity age in accordance with equations (4), (5), and (6), after replacing the PAL value in these equations with a value corrected based on the length of time that the pedometer 100 is worn in accordance with equation (9), an activity age that is comparatively close to when the pedometer 100 is worn all day can be computed even if the length of time worn is less than 1 day, and the user can gain the motivation to be active.

The physical activity level PAL computed when subjects wore the pedometer 100 for 24 hours during normal daily life was 1.75. The physical activity level PAL computed when subjects similarly wore the pedometer 100 for 10 hours during normal daily life was 1.65. From these test results, the coefficient k5 can be determined to be (1.75−1.65)/(24−10)=0.0071.

Computation of Activity Age for 1 Week

With the abovementioned method for computing the activity age according to a preferred embodiment of the present invention, since the computation is based on the total calories burned for 1 day, the activity age increases greatly particularly on days on which the user does not exercise, and conversely decreases greatly on days on which the user exercises, making it difficult for the user to stay motivated.

In view of this, it is arguably desirable to compute the activity age based on the activity content for a fixed period of 2 days or more, such as the "23 Ex or more per week" exercise standard in units of 1 week provided by the Ministry of Health, Labour and Welfare, for example.

Thus, the average value in day units is computed from the total calories burned for a fixed period (e.g., 1 week or the current week), and the activity age is computed from the computed average value. In the case where, however, the pedometer 100 is only worn for a short time during the fixed period or where there are days on which the user forgets to wear the pedometer 100, the average value thus decreases markedly and the activity age increases, adversely influencing the user's motivation. As a countermeasure to this, in the case where the length of time worn on 1 day measured from the acceleration signal is less than a fixed time period (e.g., less than 6 hours), the average value is computed excluding the total calories burned on that day.

If the number of days, during the fixed period, on which the pedometer 100 is worn for 6 hours or more is given as N [day], the activity age A can be computed by the following equation (10).

activity age $A$=real age+$k6$×{$NC$−(1.75×basal metabolic rate×$N$)} (10).

The variable NC corresponds to the total calories burned during the N days. The coefficient k6 is read out from the coefficient data group 51. Here, because the coefficient k6 is stored in the coefficient data group 51 for each set of weight W, height H, and gender F, the coefficient varying unit 14 is able to read out the corresponding correction coefficient k6, by searching the coefficient data group 51 based on the user's weight, height, and gender read out from the memory 50.

The activity age acquisition unit 13 is arranged and programmed to compute the activity age A by equation (10), and computes the activity age in accordance with the abovementioned processing procedure (for standardization by real age) using the activity age A. In other words, the activity age acquisition unit 13 computes the activity age by equation (4), together with computing the activity age using the activity age A computed by equation (10) and equations (7) and (8).

As a result, by targeting the user's activity during a fixed period, an index that is useful even to a user who has particular exercise habits, such as, for example, doing a lot of exercise on Saturdays and Sundays to bring his or her activity age for that period back to near his or her real age despite not doing much exercise during the week.

Standardization of Activity Age by 23 Ex/Week

It is desirable to compute activity age in conjunction with a recommended level of activity intensity. While the Exercise Guide 2006 issued by the Ministry of Health, Labour and Welfare promotes exercise by presenting a 23 Ex/week guideline for prevention of lifestyle-related diseases and maintenance of health, the guideline is not taken into consideration in the abovementioned procedures for computing the activity age. Thus, even if the user exercises every day at a pace at which he or she does 23 Ex or more per week, for example, the activity age may become much higher than the real age. Accordingly, in order for the user to feel a sense of accomplishment from exercising, it is desirable for the activity age to be computed so as to be consistent with the guideline.

In view of this, in the present preferred embodiment, the target-based varying unit 17 is arranged and programmed to compute the activity age using an equation that gives activity age≈real age at an exercise level of "23 Ex per week". Note that the target value is not limited to 23 Ex, and a configuration may be adopted in which the target value can be changed via the operation unit 30. For example, in the case of a male user who is 50 years old, 170 cm, 60 kg, and has a basal metabolic rate of 1374 kcal, the total calories burned per week and the total calories burned per day targeted following from the abovementioned guideline can be computed by equations (11) and (12).

target calories burned/week=1.05×60 [kg]×23 [Ex]
=1449 [kcal] (11).

target calories burned/day=1449 [kcal]/7 [day]=207 [kcal] (12).

Standard PAL=(1374 [kcal]+207 [kcal])/1374 [kcal]=1.15 is computed. Accordingly, following from the guideline, a conversion equation (13) that given activity age≈real age at PAL=1.15 is applied. The coefficient k7 in equation (13) is read out from the coefficient data group 51.

Here, because the coefficient k7 is stored in the coefficient data group 51 for each set of real age R, weight W, height H, basal metabolic rate, and gender F, the target-based varying unit 17 is arranged and programmed to read out the corresponding correction coefficient k7, by searching the coefficient data group 51 based on the user's real age, weight, height, basal metabolic rate, and gender read out from the memory 50.

The activity age acquisition unit 13 computes the activity age A by activity age A=real age+k7×{total calories burned−(1.15×basal metabolic rate)} (eq. (13)), and computes the activity age in accordance with the abovementioned processing procedure (standardization by real age) to use this activity age A. In other words, the activity age acquisition unit 13 computes the activity age by equation (4), together with computing the activity age using the activity age A computed by equation (13) and the abovementioned equations (7) and (8).

As a result, activity age real age if the user exercises at a pace that achieves 23 Ex per week, and the computed activity age serves as an index that is useful as a guide to achieve 23 Ex per week.

Computation of Activity Age Based on BMI (Body Mass Index)

An index of the user's physique is not taken into consideration in the above-mentioned computation of activity age. A physique index is an index indicating a balance of the user's physique. Here, BMI representing a person's body mass computed from the relationship between weight and height included in the body information is introduced as a physique index. BMI=(weight (kg)/(height (m)×height (m))) is computed. BMI is known to be strongly correlated with the amount of body fat, and a height and a weight that give BMI=22 are assumed to be ideal, that is, values that minimize illness. A computation equation (14) used to computer the activity age using this value 22 and the user's BMI is shown below. The user's BMI can be computed using the physique data 57.

activity age=$R$+$k8$×[(total calories burned at standard level/22)−(computed total calories burned/BMI)] (14).

"Total calories burned at standard level" in equation (14) can be computed by the relational equation (total calories burned [kcal/day] at standard level=theoretical basal metabolic rate [kcal/day]×1.75) as mentioned above. The coefficient k8 is 0.087, for example. Here, because the coefficient k8 is stored in the coefficient data group 51 for each set of BMI and the gender F, the coefficient varying unit 14 is able to read out the corresponding correction coefficient k8 from the memory 50, by searching the coefficient data group 51 based on the user's BMI and gender. The activity age acquisition unit 13 computes the activity age using equation (14).

Computation of activity age that takes a physique index such as the amount of body fat of the user into consideration is thereby possible, and the computed activity age can be provided as a useful index.

The above-mentioned processing in computing the activity age may be implemented by the device 200. In other words, the device 200 is preferably arranged and programmed to store the data of the areas E2 and E3 in the memory 202, and to receive the activity intensity data Mi from the pedometer 100. The CPU 201 thus computes the activity age with the abovementioned computation procedures using this data, and outputs the computed activity age to the output unit 203 or transmits the computed activity age to the pedometer 100 to be displayed on the display 20.

Also, the activity age computed daily may be stored in the memory 50 (or the memory 202), and may be presented by time-series trend display on demand. The user is able to check for changes in activity amount by the change in activity age from the trend display, enabling the user to be provided with a clear motivation to be active.

Modifications of Preferred Embodiments

An appropriate method of computing the activity age to use can be selected from the above-mentioned preferred embodiments of methods by a user operation via the operation unit 30. Also, activity age may be computed by combining two or more of the computation methods.

The activity intensity may alternatively be computed by a method using heart rate detected from the user and a predetermined arithmetic equation, instead of being computed by the abovementioned method based on body motion detected in accordance with the acceleration signal.

Also, although the basal metabolic rate is preferably computed using equation (1), the computation method is not limited thereto. For example, the basal metabolic rate may alternatively be computed from the body composition information measured by the weight/body composition measurement unit 301. As for a preferred embodiment of a method of computing the basal metabolic rate from body composition information, the basal metabolic rate can be easily computed from fat-free mass measured by the weight/body composition measurement unit 301. In this case, the basal metabolic rate can be computed in accordance with the equation: basal metabolic rate=A×FFM+B (FFM: fat-free mass, A, B: constants).

Other Preferred Embodiments

A preferred embodiment of a method for computing and outputting the activity age described using the abovementioned flowchart can also be provided as a program. The program for realizing the method is stored on a non-transitory computer readable medium included in the memory 50 of the pedometer 100 in advance, and the processing is realized by the CPU 10 which is arranged and programmed to read out the program from the memory 50 and execute the instruction code. This program may alternatively be supplied by being downloaded from an external information processing device including the device 200 to a non-transitory computer readable medium included in the memory 50 via the communication I/F 60 through a communication line.

Also, the device 200 may store such a program and the data shown in FIG. 4 in the memory 202, the activity age may be computed in the device 200 by the CPU 201 reading out the program from the memory 202 and executing the instruction code, and the computed activity age may be displayed via the output unit 203. The data shown in FIG. 4 can be transmitted from the pedometer 100 to the device 200 via the communication I/F 60. Also, the activity age computed by the device 200 may be transmitted to the pedometer 100 and displayed on the display 20.

To allow the device 200 to compute the activity age, the program is preferably provided to the device 200 as a program product recorded on a non-transitory computer-readable recording medium (not shown) that is attached to the device 200 such as, for example, a floppy disk, the CD-ROM 206, a ROM (Read Only Memory) of the memory 202, a RAM (Random Access Memory), or a memory card. Alternatively, the program can also be provided by prerecording the program on a non-transitory recording medium such as a hard disk (not shown) built into the device 200. Also, the program can also be provided by download to a non-transitory computer readable medium included in the device 200 from other information processing device via a network.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. An activity meter comprising:
an activity amount acquisition unit arranged and programmed to acquire an activity amount indicating an amount of physical activity of a user;
an activity age acquiring unit arranged and programmed to acquire an activity age representing a standard age of a person who does a same amount of activity as the activity amount acquired in a unit period, using body information and a basal metabolic rate of the user; and
an output unit arranged and programmed to output information relating to the activity age; wherein
the activity amount acquisition unit includes at least one of an accelerometer, a pedometer, and a heart rate monitoring device;
the activity age acquiring unit is arranged and programmed to compute the activity age in accordance with an arithmetic equation that uses the body information and the basal metabolic rate of the user;
the arithmetic equation includes a coefficient; and
the activity age acquiring unit is arranged and programmed to variably determine the coefficient such that a ratio between an amount of fluctuation in the basal metabolic rate and an amount of fluctuation in the activity age computed in response to the amount of fluctuation in the basal metabolic rate is a value in a predetermined range.

2. The activity meter according to claim 1, further comprising:
a calorie computing unit arranged and programmed to compute calories burned by the user in the unit period, based on the activity amount acquired by the activity amount acquisition unit; and
a basal metabolic rate unit arranged and programmed to compute the basal metabolic rate of the user from the computed calories burned.

3. The activity meter according to claim 1, wherein
the body information includes a real age of the user; and
the activity age acquiring unit is arranged and programmed to determine the coefficient such that the ratio is a predetermined value, with respect to an activity age in a predetermined range that includes the real age, and determines the coefficient such that the ratio is greater than the predetermined value, with respect to an activity age that is outside the predetermined range.

4. The activity meter according to claim 1, wherein the body information includes a physique index of the user.

5. The activity meter according to claim 1, wherein
the activity amount acquisition unit includes a sensor that is worn on a body of the user and detects activity including body motion; and
the activity age acquiring unit is arranged and programmed to variably determine the coefficient in accordance with a length of time that the sensor is worn in the unit period.

6. The activity meter according to claim 1, wherein the activity age acquiring unit is arranged and programmed to variably determine the coefficient using a target activity amount for the unit period.

7. The activity meter according to claim 1, wherein
the unit period indicates 1 day; and
the calorie computing unit is arranged and programmed to compute the calories burned in the unit period from the activity amount acquired in 2 days or more.

8. An activity age management method for managing an activity age of a user with use of a processor, the method comprising the steps of:
acquiring an activity amount indicating an amount of physical activity of the user;
acquiring an activity age representing a standard age of a person who does a same amount of activity as the activity amount acquired in a unit period, using body information and a basal metabolic rate of the user; and
displaying information relating to the acquired activity age on a display; wherein
the activity amount is acquired using at least one of an accelerometer, a pedometer, and a heart rate monitoring device;
the activity age is computed in accordance with an arithmetic equation that uses the body information and the basal metabolic rate of the user;
the arithmetic equation includes a coefficient; and
the coefficient is variably determined such that a ratio between an amount of fluctuation in the basal metabolic rate and an amount of fluctuation in the activity age computed in response to the amount of fluctuation in the basal metabolic rate is a value in a predetermined range.

9. A non-transitory computer readable medium including a program causing a processor to execute an activity age management method, the activity age management method comprising the steps of:
acquiring an activity amount indicating an amount of physical activity of a user;
acquiring an activity age representing a standard age of a person who does a same amount of activity as the activity amount acquired in a unit period, using body information and a basal metabolic rate of the user; and
displaying information relating to the acquired activity age on a display; wherein
the activity amount is acquired using at least one of an accelerometer, a pedometer, and a heart rate monitoring device;
the activity age is computed in accordance with an arithmetic equation that uses the body information and the basal metabolic rate of the user;
the arithmetic equation includes a coefficient; and
the coefficient is variably determined such that a ratio between an amount of fluctuation in the basal metabolic rate and an amount of fluctuation in the activity age computed in response to the amount of fluctuation in the basal metabolic rate is a value in a predetermined range.

10. An activity age management system comprising a measurement device that measures an amount of activity of a user and an information processing device, the measurement device including:
an activity intensity measuring unit arranged and programmed to measure an activity intensity of the user; and
a measurement output unit arranged and programmed to output measurement data in which the activity intensity is associated with a measurement date-time; wherein
the information processing device includes:
a measurement receiving unit arranged and programmed to receive the measurement data output from the measurement device;
an activity amount acquiring unit arranged and programmed to acquire an activity amount in a unit period, based on the measurement data;
an activity age acquiring unit arranged and programmed to acquire an activity age representing a standard age of a person who does a same amount of activity as the activity amount acquired in the unit period, using body information and a basal metabolic rate of the user; and
an information output unit arranged and programmed to output information relating to the activity age; wherein
the activity age acquiring unit is arranged and programmed to compute the activity age in accordance with an arithmetic equation that uses the body information and the basal metabolic rate of the user;
the arithmetic equation includes a coefficient; and
the activity age acquiring unit is arranged and programmed to variably determine the coefficient such that a ratio between an amount of fluctuation in the basal metabolic rate and an amount of fluctuation in the activity age computed in response to the amount of fluctuation in the basal metabolic rate is a value in a predetermined range.

* * * * *